United States Patent
Zhang et al.

(10) Patent No.: US 11,396,518 B2
(45) Date of Patent: Jul. 26, 2022

(54) SOLID FORMS OF THIOPHENE DERIVATIVES

(71) Applicant: TIANJIN HEMAY PHARMACEUTICAL CO., LTD., Tianjin (CN)

(72) Inventors: Donglei Zhang, Tianjin (CN); Liyu Wang, Tianjin (CN); Xingwen Li, Tianjin (CN)

(73) Assignee: TIANJIN HEMAY PHARMACEUTICAL CO., LTD., Tianjin (CN)

( * ) Notice: Subject to any disclaimer, the term of this patent is extended or adjusted under 35 U.S.C. 154(b) by 0 days.

(21) Appl. No.: 17/052,077

(22) PCT Filed: Apr. 30, 2019

(86) PCT No.: PCT/CN2019/085352
§ 371 (c)(1),
(2) Date: Oct. 30, 2020

(87) PCT Pub. No.: WO2019/210867
PCT Pub. Date: Nov. 7, 2019

(65) Prior Publication Data
US 2021/0380600 A1      Dec. 9, 2021

(30) Foreign Application Priority Data
May 2, 2018   (CN) ............................. 201810407741

(51) Int. Cl.
*C07D 495/04*      (2006.01)

(52) U.S. Cl.
CPC ........ *C07D 495/04* (2013.01); *C07B 2200/13* (2013.01)

(58) Field of Classification Search
CPC .......................... C07D 495/04; C07B 2200/13
See application file for complete search history.

(56) References Cited

U.S. PATENT DOCUMENTS

| | | | |
|---|---|---|---|
| 6,011,050 A | 1/2000 | Muller et al. | |
| 2018/0354967 A1* | 12/2018 | Sullivan | ............... C07D 495/04 |

FOREIGN PATENT DOCUMENTS

| | | |
|---|---|---|
| CN | 101186612 A | 5/2008 |
| CN | 101885731 A | 11/2010 |
| WO | WO-2018231604 A1 | 12/2018 |
| WO | WO-201902903 A1 | 1/2019 |

OTHER PUBLICATIONS

International Search Report and Written Opinion for International application No. PCT/CN2019/085352, dated Jul. 25, 2019, with English Language Translation, 8 pages.

* cited by examiner

*Primary Examiner* — Timothy R Rozof
(74) *Attorney, Agent, or Firm* — Goodwin Procter LLP

(57) ABSTRACT

Disclosed is an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide.

20 Claims, 4 Drawing Sheets

SOLID FORMS OF THIOPHENE DERIVATIVES

CROSS-REFERENCE TO RELATED APPLICATIONS

This application is a U.S. national stage application filed under 35 U.S.C. § 371 of International Application No. PCT/CN2019/085352, filed Apr. 30, 2019, which claims priority to and the benefit of Chinese Patent Application No. 201810407741.X filed May 2, 2018, the contents of each of which are hereby incorporated by reference herein in their entirety.

FIELD

The present disclosure generally relates to the field of organic chemistry and medicinal chemistry.

BACKGROUND

PDE-4 enzyme inhibitors are effective on various inflammatory diseases in clinical, including asthma, chronic obstructive pulmonary disease (COPD), allergic rhinitis, allergic dermatitis and the like. PDE-4 enzyme inhibitors are also effective on various diseases including arthritis, sepsis and the like on animal models.

SUMMARY

In one aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide, having an X-ray powder diffraction (XRPD) pattern substantially as shown in FIG. 1.

In another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially free of solvent, having an X-ray powder diffraction (XRPD) pattern substantially as shown in FIG. 1.

In still another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially free of water, having an X-ray powder diffraction (XRPD) pattern substantially as shown in FIG. 1.

In yet still another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially pure, having an X-ray powder diffraction (XRPD) pattern substantially as shown in FIG. 1.

In yet another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is free of solvent and water, having an X-ray powder diffraction (XRPD) pattern substantially as shown in FIG. 1.

In yet another aspect, the present disclosure relates to a pharmaceutical composition, comprising an amorphous solid form of compound (S)—N-[5-[1-(3-ethoxy-4-methoxyphenyl)-2-(methylsulfone)ethyl]-4,6-dioxo-5,6-dihydro-4H-thieno[3,4-c]pyrrole-1-yl]acetamide and a pharmaceutically acceptable carrier, diluent or excipient, wherein the amorphous solid form has an X-ray powder diffraction (XRPD) pattern substantially as shown in FIG. 1.

In another aspect, the present disclosure relates to a process for preparing an amorphous solid form of compound (S)—N-[5-[1-(3-ethoxy-4-methoxyphenyl)-2-(methylsulfone)ethyl]-4,6-dioxo-5,6-dihydro-4H-thieno[3,4-c]pyrrole-1-yl]acetamide, comprising dissolving (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide in ethyl acetate, and rotary evaporating solvent to obtain the amorphous solid form, wherein the amorphous solid form has an X-ray powder diffraction (XRPD) pattern substantially as shown in FIG. 1.

In another aspect, the present disclosure relates to a method for treating or preventing a disease or condition associated with PDE4 enzyme, preferably mediated by PDE4 enzyme, comprising administering a therapeutically effective amount of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide or a therapeutically effective amount of a pharmaceutical composition comprising an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide to a subject in need thereof, wherein the amorphous solid form has an X-ray powder diffraction (XRPD) pattern substantially as shown in FIG. 1.

In still another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having an X-ray powder diffraction (XRPD) pattern substantially as shown in FIG. 1.

In yet still another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having a DSC curve substantially as shown in FIG. 2 when subjected to thermal analysis using differential scanning calorimetry (DSC).

In yet still another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having a TGA curve substantially as shown in FIG. 3 when subjected to thermal analysis using thermogravimetric analysis (TGA).

In another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, wherein position and intensity of absorption peak of the amorphous solid form in an infrared (IR) spectroscopy are about as follows:

| Position of Absorption Peak (cm$^{-1}$) | Intensity of Absorption Peak (%) |
|---|---|
| 3404.3 | 72.47 |
| 3287.52 | 71.12 |
| 3084.14 | 77.6 |
| 2979.07 | 71.12 |
| 2930.92 | 69.42 |
| 1757.38 | 47.8 |
| 1701.82 | 23.97 |
| 1589.64 | 41.86 |
| 1557.48 | 49.76 |

-continued

| Position of Absorption Peak (cm$^{-1}$) | Intensity of Absorption Peak (%) |
|---|---|
| 1517.39 | 45.33 |
| 1443.03 | 66.11 |
| 1394.22 | 57.87 |
| 1372.85 | 58.51 |
| 1331.65 | 44.21 |
| 1298.07 | 31.05 |
| 1261.45 | 41.23 |
| 1240.02 | 40.44 |
| 1137.98 | 40.39 |
| 1090.98 | 51.71 |
| 1027.87 | 62.39 |
| 967.7 | 73.42 |
| 878.04 | 77.11 |
| 810.99 | 79.36 |
| 773.88 | 74.77 |
| 739.68 | 66.93 |
| 641.67 | 76.69 |
| 600.99 | 80.09 |
| 530.58 | 76.64 |
| 499.59 | 75.46 |
| 454.03 | 77.63 |

In another aspect, the present disclosure relates to a method for reducing PDE4 activity, comprising administering a therapeutically effective amount of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide or a therapeutically effective amount of a pharmaceutical composition comprising an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide to a subject in need thereof, wherein the amorphous solid form has an X-ray powder diffraction (XRPD) pattern substantially as shown in FIG. 1.

DETAILED DESCRIPTION

Figure 1:
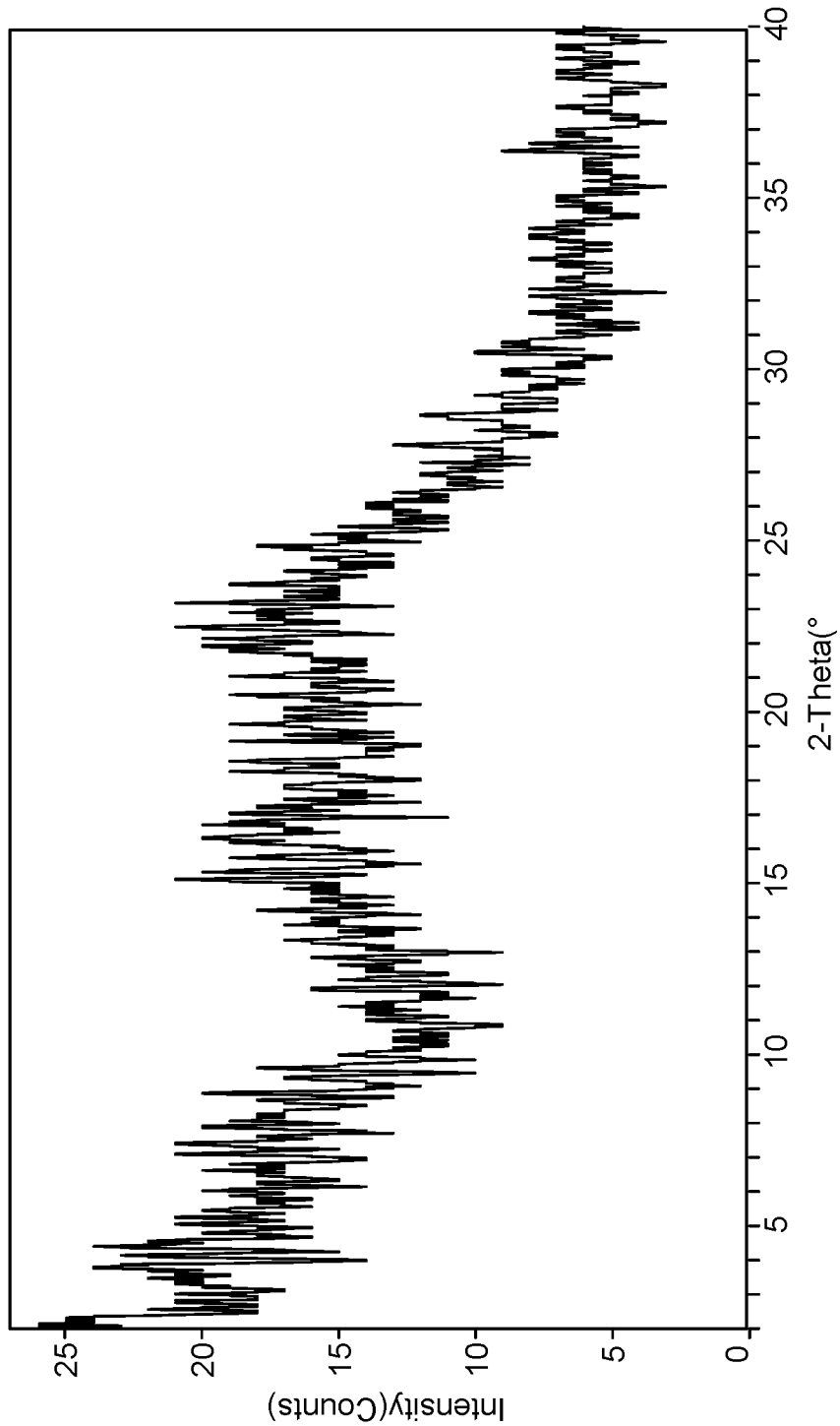
FIG. 1 shows an X-ray powder diffraction (XRPD) pattern of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure.

In the following description, certain specific details are included to provide a thorough understanding of the various disclosed embodiments. One skilled in the relevant art will recognize, however, that embodiments may be practiced without one or more of these specific details, with other methods, components, materials, etc.

Unless the context required otherwise, throughout the specification and claims which follows, the term "comprise" and variations thereof, such as "comprises" and "comprising" are to be construed in an open, inclusive sense, which is as "include, but not limited to".

As used herein and the appended claims when in use, unless the context clearly dictates otherwise, it is not singular forms include plural referents with a number indicated.

Reference throughout this specification to "one embodiment", or "an embodiment", or "in another embodiment", or "in some embodiments" means that a particular referent feature, structure or characteristic described in connection with the embodiments is included in at least one embodiment. Therefore, the appearance of the phrases "in one embodiment", or "in the embodiment", or "in another embodiment", or "in some embodiments" in various places throughout this specification are not necessarily all referring to the same embodiment. Moreover, the particular features, structures or characteristics may be combined in any suitable manner in one or more embodiments.

It is to be understood that the singular forms of articles "a", "an" and "the" as used in the specification and the appended claims of the present disclosure include plural referents unless the context clearly dictates otherwise. Thus, for example, reference to a pharmaceutical composition comprising a "pharmaceutically acceptable carrier, diluent, or excipient" includes one pharmaceutically acceptable carrier, diluent or excipient, or two or more pharmaceutically acceptable carriers, diluents or excipients.

Definition

Therefore, unless otherwise indicated, the following terms used in the specification and the appended claims have the following meanings:

In the present disclosure, the term "compound of the present disclosure" refers to (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide, which has the structure as shown below:

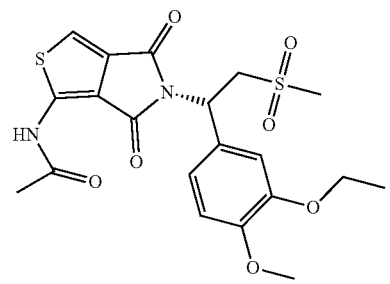

As used herein, the use of the term "about" includes and describes values or parameters per se. For example, "about X" includes and describes "X" itself. In some embodiments, the term "about" refers to a change of +/−5% when used in conjunction with or for modifying values, units, constants or numerical ranges.

As used herein, when referring to an X-ray powder diffraction (XRPD) pattern, a differential scanning calorimetry (DSC) curve, a thermogravimetric analysis (TGA) curve, an infrared (IR) spectroscopy. the term "substantially as shown in" does not necessarily refer to the same pattern and curve as those depicted in the present disclosure, but falls within the limits of experimental error or deviation when considered by one skilled in the art.

As used herein, the term "essentially identical" with reference to X-ray diffraction peak positions means that typical peak position and intensity variability are taken into account. For example, one skilled in the art will appreciate that the peak positions (2θ) will show some variability, typically as much as 0.1 to 0.2 degrees, depending on the solvents being used, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

As used herein, the term "2θ value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific polymorphic form is intended to mean the 2θ values (in degrees) as measured using the X-ray diffraction experimental conditions as described herein. For example, as described herein, CuKa (λ-1.54056 Å) was used as the source of radiation.

As used herein, In order to lattice spacing (d-spacing) of the object, the term "about" refers to ±0.1 Å.

As used herein, the term "substantially pure" refers to chemical purity and crystalline purity.

As used herein, the term "substantially free" refers to containing not more than about 20% by weight. For example, substantially free of solvent refers to containing not more than about 20% by weight of solvent. Substantially free of water refers to containing not more than 20% by weight of water.

As used herein, the term "mammal" means animals including, for example, dogs, cats, cows, sheep, horses, and humans. In some embodiments, mammals include humans.

As used herein, the term "patient" means an animal, such as a human, a companion animal, such as a dog, cat and horse, and livestock, such as cattle, swine and sheep. In some embodiments, patients are mammals, including both males and females. In some embodiments, patients are humans.

As used herein, the term "pharmaceutically acceptable" as used herein means the carrier, vehicle, diluent, excipient and/or salt must be compatible with the other ingredients of the formulation, and not deleterious to the recipient thereof other ingredients of the formulation and will not be detrimental to its recipient.

As used herein, the term "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition.

As used herein, the term "carrier" defines a compound that facilitates the incorporation of an amorphous form of a compound into cells or tissues. For example, dimethyl-sulfoxide (DMSO) is generally used as a carrier, as it facilitates the uptake of many organic compounds into cells or tissues of an organism.

As used herein, the term "pharmaceutical composition" refers to a formulation of crystal I of the compound in the present disclosure and a medium generally acceptable in the art for the delivery of the biologically active compound to mammals, e.g., humans. Such a medium includes all pharmaceutically acceptable carriers, diluents or excipients therefor.

As used herein, the term "therapeutically effective amount" refers to an amount of an amorphous solid form of the compound or combination of an amorphous solid form that ameliorates, attenuates or eliminates a particular disease or condition or a symptom of a particular disease or condition, or prevents or delays the onset of a particular disease or condition or a symptom of a particular disease or condition. The amount of an amorphous solid form of the compound of the present disclosure which constitutes a "therapeutically effective amount" will vary depending on an amorphous solid form of the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, such as a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the term "physiologically acceptable" refers to a carrier or diluent that does not eliminate the biological activities and properties of a compound.

Specific Embodiments

In one aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide, having an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide has an X-ray powder diffraction (XRPD) under CuKα radiation pattern substantially as shown in FIG. 1.

Figure 2:
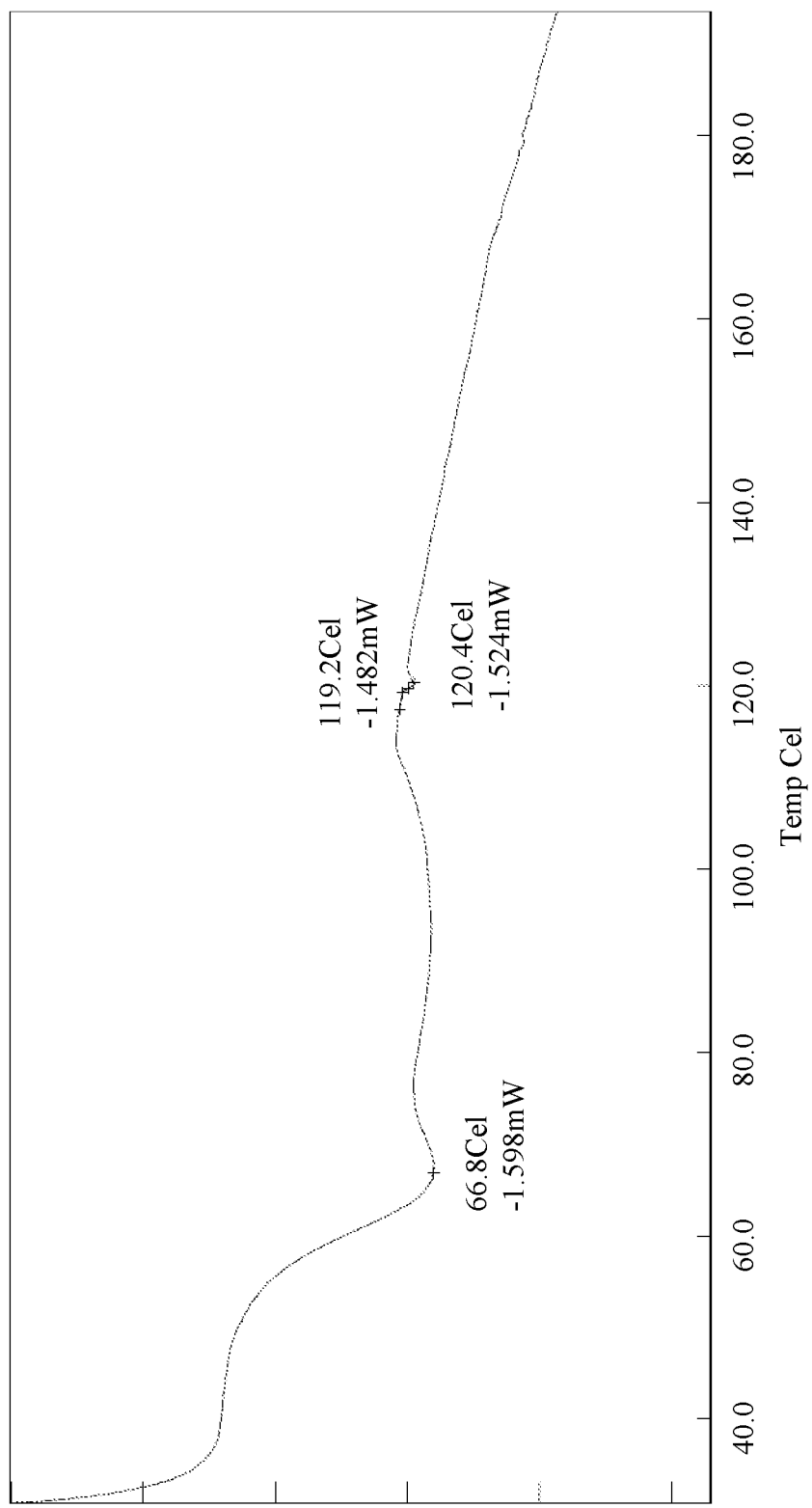
FIG. 2 shows a differential scanning calorimetry (DSC) curve of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure has a DSC curve substantially as shown in FIG. 2 when subjected to thermal analysis using differential scanning calorimetry (DSC).

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure has a DSC curve substantially as shown in FIG. 2 when subjected to thermal analysis using differential scanning calorimetry (DSC) at a heating rate of 10° C./min.

Figure 3:
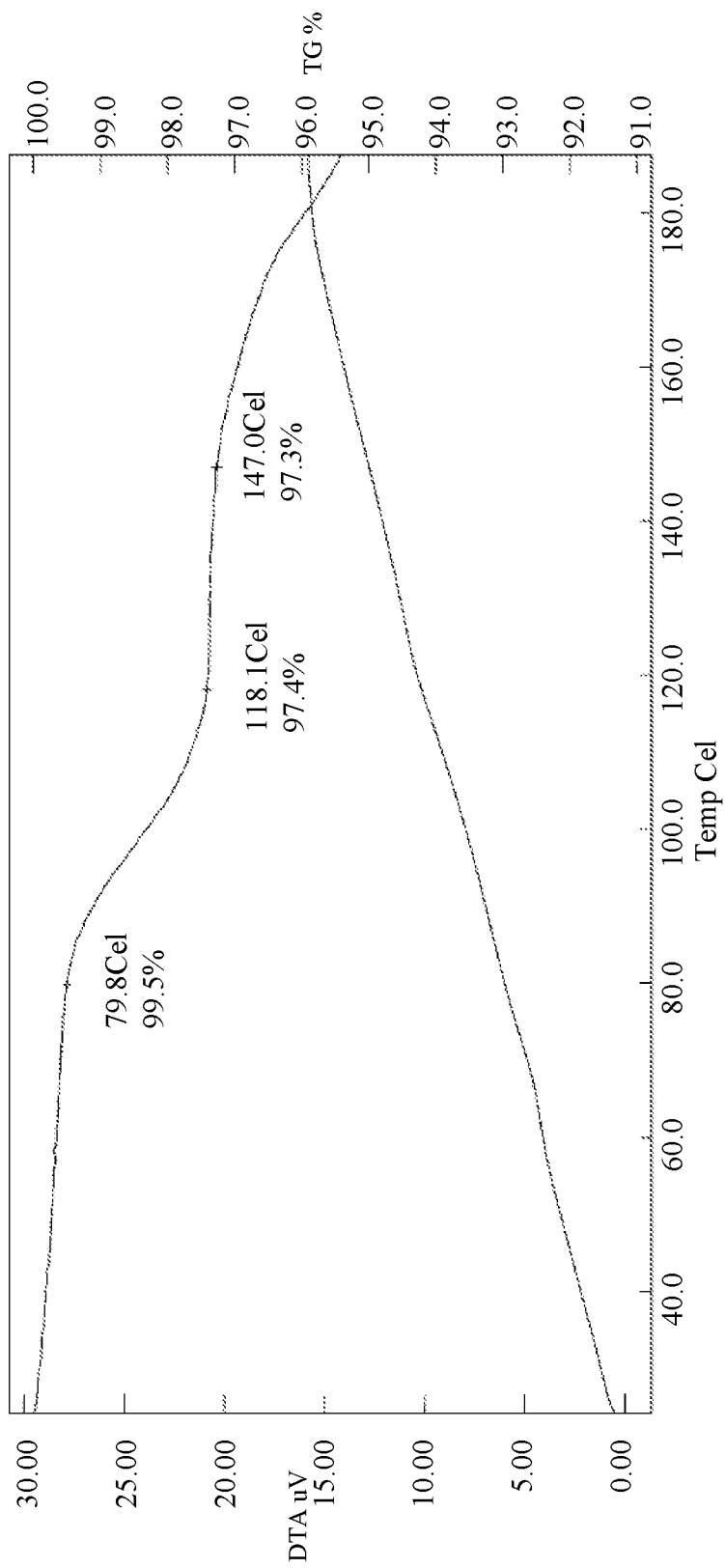
FIG. 3 shows a thermogravimetric analysis (TGA) curve of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure has a TGA curve substantially as shown in FIG. 3 when subjected to thermal analysis using thermogravimetric analysis (TGA).

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure has a TGA curve substantially as shown in FIG. 3 when subjected to thermal analysis using thermogravimetric analysis (TGA) at a heating rate of 10° C./min.

In some embodiments, position and intensity of absorption peak of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure in an infrared (IR) spectroscopy are about as follows:

| Position of Absorption Peak (cm$^{-1}$) | Intensity of Absorption Peak (%) |
|---|---|
| 3404.3 | 72.47 |
| 3287.52 | 71.12 |
| 3084.14 | 77.6 |
| 2979.07 | 71.12 |
| 2930.92 | 69.42 |
| 1757.38 | 47.8 |
| 1701.82 | 23.97 |
| 1589.64 | 41.86 |
| 1557.48 | 49.76 |
| 1517.39 | 45.33 |
| 1443.03 | 66.11 |
| 1394.22 | 57.87 |
| 1372.85 | 58.51 |
| 1331.65 | 44.21 |
| 1298.07 | 31.05 |
| 1261.45 | 41.23 |
| 1240.02 | 40.44 |
| 1137.98 | 40.39 |
| 1090.98 | 51.71 |
| 1027.87 | 62.39 |
| 967.7 | 73.42 |
| 878.04 | 77.11 |
| 810.99 | 79.36 |
| 773.88 | 74.77 |
| 739.68 | 66.93 |
| 641.67 | 76.69 |
| 600.99 | 80.09 |
| 530.58 | 76.64 |
| 499.59 | 75.46 |
| 454.03 | 77.63 |

Figure 4:
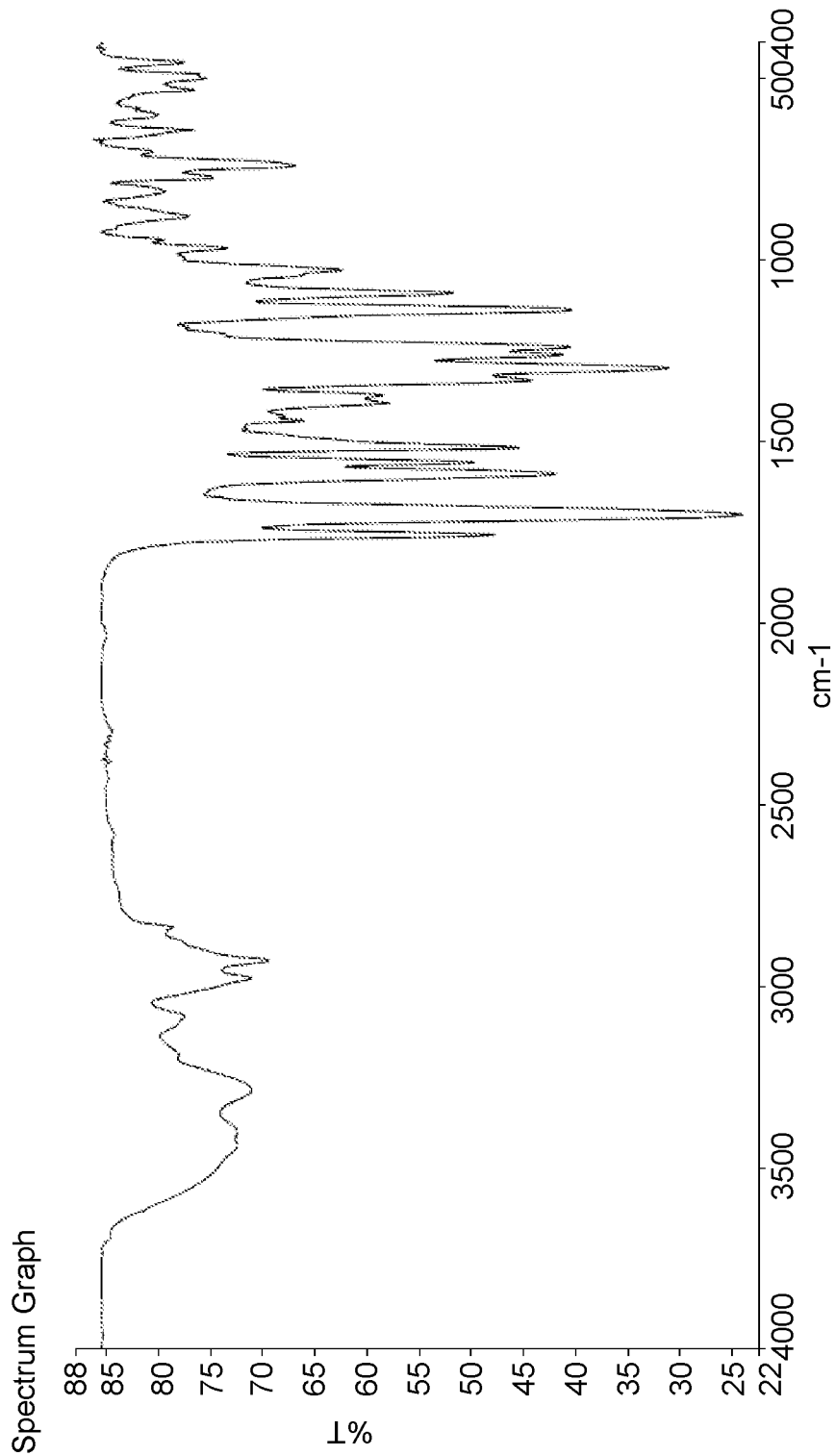
FIG. 4 shows an infrared (IR) spectroscopy of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c] pyrrole-1-yl]acetamide of the present disclosure.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure has an infrared (IR) spectroscopy substantially as shown in FIG. 4.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure compared with other solid forms has at least one advantageous property: chemical purity, fluidity, solubility, dissolution rate, morphology or crystal habit, stability such as high temperature stability, accelerated stability, illumination stability, grinding stability, pressure stability, stability in ethanol solution after equilibrium, stability in aqueous solution after equilibrium, low residual solvent content, lower hygroscopicity, fluidity, and favorable processing and treatment properties such as compressibility and bulk density.

In another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially free of solvent, having an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that substantially free of solvent has an X-ray powder diffraction (XRPD) pattern substantially under CuKα radiation as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 20% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 20% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 10% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 10% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 5% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 5% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 3% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 3% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 1% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 1% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.5% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.5% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.2% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.2% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.1% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.1% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.01% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.01% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.001% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.001% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.0001% by weight of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.0001% by weight of solvent has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is free of solvent has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is free of solvent has an X-ray powder diffraction (XRPD) pattern under CuKα radiation substantially as shown in FIG. 1.

In yet another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially free of water, having an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially free of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 20% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 20% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 10% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 10% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 5% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 5% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 3% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 3% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 1% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 1% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.5% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.5% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.2% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.2% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.1% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.1% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.01% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.01% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.001% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.001% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.0001% by weight of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that comprises not more than about 0.0001% by weight of water has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that is free of water has an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that is free of water has an X-ray powder diffraction (XRPD) pattern under CuKα radiation substantially as shown in FIG. 1.

In some embodiments, weight loss of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure is not more than 5% when the amorphous solid form is heated to decompose during thermal analysis using thermogravimetric analysis (TGA) at a heating rate of 10° C./min.

In some embodiments, weight loss of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure is not more than 2% when the amorphous solid form is heated to decompose during thermal analysis using thermogravimetric analysis (TGA) at a heating rate of 10° C./min.

In some embodiments, weight loss of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure is not more than 1% when the amorphous solid form is heated to decompose during thermal analysis using thermogravimetric analysis (TGA) at a heating rate of 10° C./min.

In some embodiments, weight loss of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure is not more than 0.5% when the amorphous solid form is heated to decompose during thermal analysis using thermogravimetric analysis (TGA) at a heating rate of 10° C./min.

In another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is substantially pure, having an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that is substantially pure has an X-ray powder diffraction (XRPD) pattern under CuKα radiation substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that is substantially pure comprises at least about 95% by weight, preferably at least about 98% by weight, more preferably at least about 99% by weight of the amorphous solid form and less than about 5% by weight, preferably less than about 2% by weight, more preferably less than about 1% by weight of other compounds having structures different from the chemical structure of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure that is substantially pure comprises at least about 95% by weight, preferably at least about 98% by weight, more preferably at least about 99% by weight of the amorphous solid form and less than about 5% by weight, preferably less than about 2% by weight, more preferably less than about 1% by weight of other crystal forms of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure. This means an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of the present disclosure comprises less than about 5% by weight of other compounds and less than about 5% by weight of any other forms (also referred to as "phase uniformity").

In yet another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is free of solvent and water, having an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide that is free of solvent and water has an X-ray powder diffraction (XRPD) pattern under CuKα radiation substantially as shown in FIG. 1.

In yet another aspect, the present disclosure relates to a pharmaceutical composition comprising an amorphous solid form of compound (S)—N-[5-[1-(3-ethoxy-4-methoxyphenyl)-2-(methylsulfone)ethyl]-4,6-dioxo-5,6-dihydro-4H-thieno[3,4-c]pyrrole-1-yl]acetamide and a pharmaceutically acceptable carrier, diluent or excipient, wherein the amorphous solid form has an X-ray powder diffraction (XRPD) pattern substantially as shown in FIG. 1.

In some embodiments, the pharmaceutical composition of the present disclosure is formulated as tablet, solution, granule, patch, ointment, gel, capsule, aerosol or suppository administered via parenteral, transdermal, mucosa, nasal, buccal, sublingual or oral route.

Pharmaceutical Composition

In some embodiments, the pharmaceutical composition comprises an amorphous solid form of the compound as disclosed herein, and a pharmaceutically acceptable carrier, diluent, or excipient.

In some embodiments, the route of administration of an amorphous solid form for treating or preventing a disease associated with PDE4 enzyme, preferably mediated by PDE4 enzyme to the mammals can be non-parenteral route.

In some embodiments, the route of administration of an amorphous solid form for treating or preventing a disease associated with PDE4 enzyme, preferably mediated by PDE4 enzyme to the mammals can be oral route.

In some embodiments, the route of administration of an amorphous solid form for treating or preventing a disease associated with PDE4 enzyme, preferably mediated by PDE4 enzyme to the mammals can be intrarectal route.

The compound as described herein may be obtained in any suitable form such as tablet, capsule, powder, oral solution, suspension, patch, ointment, gel, capsule, aerosol, suppository and the like. Exemplary examples of tablets comprise, but are not limited to, plain tablets, sugar-coated tablets and film-coated tablets.

Examples of a pharmaceutically acceptable carrier that can be used in the pharmaceutical composition of the present disclosure include, but are not limited to, any adjuvant, carrier, excipient, glidant, sweetening agent, diluent, preservative, dye/colorant, flavor enchancer, surfactant, wetting agent, dispersing agent, suspending agent, stabilizer, isosmotic agent, solvent or emulsifier, which has been approved by the United States Food and Drug Administration as being acceptable for use in humans or animals. Acceptable carriers or diluents for therapeutic use are well-known in the art, and are described, for example, in Remington's Pharmaceutical Sciences, 18th Ed., Mack Publishing Co., Easton, Pa. (1990), which is incorporated herein by reference in its entirety.

The pharmaceutical compositions of the present disclosure may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. The route of administration can be non-parenteral route, oral route and intrarectal route. The dosage administered will be dependent upon the age, health, and weight of the recipient, kind of concurrent treatment, if any, frequency of treatment, and the nature of the effect desired.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art.

Particularly suitable for oral use are ordinary tablets (plain tablets), sugar-coated tablet, film-coated tablets, pills, coated tablets, capsules, powders, granules, syrups, juices or drops, suitable for rectal use are suppositories, suitable for parenteral use are solutions, or oil-based or aqueous solutions, furthermore suspensions, emulsions or implants, and suitable for topical use are ointments, creams or powders. The compounds of the present disclosure may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

In some embodiments, a pharmaceutical composition of the present disclosure is formulated as tablet, solution, granule, patch, ointment, capsule, aerosol or suppository administered via parenteral, transdermal, mucosa, nasal, buccal, sublingual or oral route.

Preservatives, stabilizers, dyes, sweeteners, flavoring agents, fragrances, and the like, may be provided in the pharmaceutical composition. For example, sodium benzoate, ascorbic acid and esters of p-hydroxybenzoic acid may be added as preservatives. Furthermore, antioxidants and suspending agents may be used.

In various embodiments, alcohols, esters, sulfating aliphatic alcohols, and the like may be used as surfactants; sucrose, glucose, lactose, starch, crystalline cellulose, mannitol, light anhydrous silicate, magnesium aluminate, methyl magnesium silicate aluminate, synthetic aluminum silicate, calcium carbonate, calcium bicarbonate, calcium hydrogenphosphate, calcium hydroxymethyl cellulose and the like may be used as excipients; magnesium stearate, talc, hardened oil may be used as smoothing agents; coconut oil, olive oil, sesame oil, peanut oil, soybean may be used as suspending agents or lubricants; cellulose acetate phthalate as a derivative of a carbohydrate such as cellulose or sugar, or methylacetate-methacrylate copolymer as a derivative of polyethylene may be used as suspending agents; and plasticizers such as ester phthalates and the like may be used as suspending agents.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal or intraocular injections. The compound can be administered in sustained or controlled release dosage forms, including depot injections, osmotic pumps, pills, transdermal (including electromigrating) patches, and the like for prolonged and/or timed, pulsed administration at a predetermined rate.

Pharmaceutical compositions of the present disclosure may be manufacture in manner that is itself known, for example, by means of conventional mixing, dissolving, granulating, dragee-making, levigating, emulsifying, encapsulating, entrapping, or tabletting processes.

Pharmaceutical compositions for use in accordance with the present disclosure thus may be formulated by a conventional manner using one or more physiologically acceptable carriers comprising excipients and auxiliaries which facilitate processing the active compounds into preparation which can be used pharmaceutically. Proper formulation is dependent on the route of administration chosen. Any of the well-known techniques, carriers and excipients may be used as suitable and as understood in the art.

Injectables can be prepared in conventional forms, either as liquid solutions or suspensions, solid forms suitable for solution or suspension in liquid prior to injection, or as emulsions. Suitable excipients are, for example, water, saline, glucose, mannitol, lactose, lecithin, albumin, sodium glutamate, cysteine hydrochloride, and the like. Furthermore, if desired, the injectable pharmaceutical compositions may contain minor amounts of nontoxic auxiliary substances, such as wetting agents, pH buffering agents, and the like. Physiologically compatible buffers include, but are not limited to, Hank's solution, Ringer's solution or physiological saline buffer. If desired, absorption enhancing preparations (such as liposomes) may be used.

For oral administration, the compound can be formulated readily by combining the active compound with pharmaceutically acceptable carriers well known in the art. Such carriers enable the compound of the disclosure to be formulated as tablets, pills, dragees, capsules, liquids, gels, syrups, ointments, suspensions, and the like, for oral ingestion by a patient to be treated. Pharmaceutical preparation for oral use can be obtained by combining the active compound with solid excipient, optionally grinding a resultant mixture, and processing the mixture of granules, after adding suitable auxiliaries, if desired, to obtain tablets or dragee cores. Suitable excipients are, in particular, fillers such as sugars, including lactose, saccharose, mannitol or sorbitol; cellulose preparations such as, for example, maize starch, wheat starch, rice starch, potato starch, gelatin, gum tragacanth, methylcellulose, hydroxypropyl methylcellulose, sodium carboxymethylcellulose, and/or polyvinylpyrrolidone (PVP). If desired, disintegrating agents may be added, such as the crosslinked polyvinylpyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures. Dyestuffs or pigments may be added into the tablets or dagree coatings for identification or to characterizing different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures.

Pharmaceutical preparations which can be used orally include push-fit capsules made of gelatin, as well as soft, sealed capsules made of gelatin and a plasticizer such as glycerol or sorbitol. The push-fit capsules can contain active ingredients in admixture with filler such as sugar, binders such as starches, and/or lubricants such as talc or magnesium stearate and, optionally, stabilizers. In soft capsules, the active ingredients may be dissolved or suspended in suitable liquids, such as fatty oil, liquid paraffin, or liquid polyethylene glycols. Furthermore, stabilizers may be added. All formulations for oral administration should be in dosages suitable for such administration.

In some embodiments, the pharmaceutical composition of the present disclosure may comprise 0.1%-95% of an amorphous solid form of the compound as disclosed herein.

In some embodiments, the pharmaceutical composition of the present disclosure may comprise 1%-70% of an amorphous solid form of the compound as disclosed herein.

Under any circumstances, the composition or formulation to be administered may comprise some amount of an amorphous solid form of the compound as disclosed herein, which is effective to treat the disease/condition of a study subject to be treated.

In another aspect, the present disclosure relates to a process for preparing an amorphous solid form of compound (S)—N-[5-[1-(3-ethoxy-4-methoxyphenyl)-2-(methylsulfone)ethyl]-4,6-dioxo-5,6-dihydro-4H-thieno[3,4-c]pyrrole-1-yl]acetamide, comprising dissolving (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide in ethyl acetate, and rotary evaporating solvent to obtain the amorphous solid form, wherein the amorphous solid form has an X-ray powder diffraction (XRPD) pattern substantially as shown in FIG. 1.

In some embodiments, (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide is dissolved in ethyl acetate until completely dissolved and is filtered. The filtrate is heated to 45° C. to 55° C. and rotary evaporated under vacuum degree of 0.1 MPa to obtain the amorphous solid form.

In some embodiments, (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide is dissolved in ethyl acetate until completely dissolved and is filtered. The filtrate is heated to 50° C. and rotary evaporated under vacuum degree of 0.1 MPa to obtain the amorphous solid form.

In some embodiments, (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide is dissolved in ethyl acetate, heated to 40° C., stirred until completely dissolved and is filtered. The filtrate is heated to 50° C. and rotary evaporated under vacuum degree of 0.1 MPa to obtain the amorphous solid form.

In another aspect, the present disclosure relates to a method for treating or preventing a disease or condition associated with PDE4 enzyme, preferably mediated by PDE4 enzyme, comprising administering a therapeutically effective amount of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide or a therapeutically effective amount of a pharmaceutical composition comprising an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide to a subject in need thereof, wherein the amorphous solid form has an X-ray powder diffraction (XRPD) pattern substantially as shown in FIG. 1.

In some embodiments, the subject is a mammal.

In some embodiments, the subject is a human.

Exemplary examples of diseases or conditions that can be used in the present disclosure include, but are not limited to, inflammatory diseases or conditions, infectious diseases or conditions, immunological diseases or conditions, and cancer diseases or conditions.

In some embodiments, exemplary examples of the diseases or conditions include, but are not limited to, head carcinoma, thyroid carcinoma, neck cancer, eye cancer, skin cancer, oral cancer, throat cancer, esophagus cancer, breast cancer, bone cancer, leukemia, myeloma, lung cancer, colon cancer, carcinoma of sigmoid, rectal cancer, gastric cancer, prostate cancer, breast cancer, ovarian cancer, kidney cancer, liver cancer, pancreatic cancer, brain cancer, intestinal cancer, heart cancer, adrenal carcinoma, subcutaneous tissue cancer, lymph node cancer, malignant melanoma, malignant glioma, HIV, hepatitis, adult respiratory distress syndrome, bone absorption disease, chronic obstructive pulmonary disease, chronic pneumonia, dermatitis, inflammatory skin disease, atopic dermatitis, cystic fibrosis, septic shock, pyaemia, endotoxin shock, blood dynamic shock, septic disease syndrome, ischemia reperfusion injury, meningitis, psoriasis, fibrosis disease, cachexia, graft rejection of graft versus host disease, autoimmunity disease, rheumatoid spondylitis, arthritis symptom (such as rheumatoid arthritis or osteoarthritis), osteoporosis, Crohn's disease, ulcerative colitis, enteritis, multiple sclerosis, systemic lupus erythematosus, erythema nodosum leprosum of leprosy (ENL), radiation damage, asthma, oxygen enriched lung injury, microorganism infections and microorganism infection syndrome.

In some embodiments, a method for treating or preventing a disease or condition associated with PDE4 enzyme, preferably mediated by PDE4 enzyme, comprising administering 1 mg to 10 g of an amorphous solid form of the compound as disclosed herein to a subject in need thereof.

In some embodiments, a method for treating or preventing a disease or condition associated with PDE4 enzyme, preferably mediated by PDE4 enzyme, comprising administering 10 mg to 3000 mg of an amorphous solid form of the compound as disclosed herein to a subject in need thereof.

In some embodiments, a method for treating or preventing a disease or condition associated with PDE4 enzyme, preferably mediated by PDE4 enzyme, comprising administering 1 mg to 200 mg of an amorphous solid form of the compound as disclosed herein to a subject in need thereof.

In some embodiments, a method for treating or preventing a disease or condition associated with PDE4 enzyme, preferably mediated by PDE4 enzyme, comprising administering 1 mg, 5 mg, 10 mg, 30 mg, 40 mg, 50 mg, 60 mg, 70 mg, 90 mg, 100 mg, 120 mg, 150 mg, or 200 mg of an amorphous solid form of the compound as disclosed herein to a subject in need thereof.

Methods of Administration

At least one of an amorphous solid form of the compound of the present disclosure or the pharmaceutical compositions comprising at least one of an amorphous solid form of the compound of the present disclosure may be administered to the patient by any suitable means and/or by any means that topically delivers an amorphous solid form of the compound of the present disclosure. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing an amorphous solid form of the compound of the present disclosure into contact with living tissue. For example, transdermal administration, which includes administration in an ointment, cream, gel, aerosol, suspension, emulsion, or other such forms.

The most suitable route depends on the nature and severity of the condition to be treated. A person having ordinary skill in the art also knows determination of methods of administration (buccal, intravenous, inhalation subcutaneous, rectal and the like), dosage form, suitable pharmaceutical excipients and other events regarding delivering the solid forms of the compound to a subject in need thereof.

Pharmaceutical compositions suitable for administration include compositions where the active ingredients are contained in an amount effective to achieve its intended purpose. The therapeutically effective amount of the pharmaceutical composition disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of solid form of the compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular forms of the compounds employed, and the specific use for which these forms of the compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 μg/kg and 1000 mg/kg body weight, in some embodiments, between about 100 μg/kg and 300 mg/kg body weight. Alternatively, dosages may be based and calculated upon the surface area of the patient, as understood by those of skill in the art.

The exact formulation, route of administration and dosage for the pharmaceutical compositions of the present disclosure can be chosen by the individual physician in view of the patient's condition. Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and 500%, in some embodiments, between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, in some embodiments, between 1 mg and 2000 mg, e.g. 5 to 1500 mg. In other embodiments, an intravenous, subcutaneous, or intramuscular dose of each active ingredient of between 0.01 mg and 1000 mg, in some embodiments, between 0.1 mg and 1000 mg, e.g. 1 to 800 mg is used. In cases of administration of a pharmaceutically acceptable salt, dosages may be calculated as the free base. In some embodiments, the composition is administered 1 to 4 times per day. Alternatively, the compositions of the disclosure may be administered by continuous intravenous infusion, in some embodiments, at a dose of each active ingredient up to 2000 mg per day. As will be understood by those of skill in the art, in certain situations it may be necessary to administer the compounds disclosed herein in amounts that exceed, or even far exceed, the above-stated dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, in some embodiments, between 30-90% and in some embodiments, between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and in some embodiments, human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the State Food and Drug Administration or the U.S. Food and Drug Administration for prescription drugs, or the approved product insert. Compositions comprising a compound of the disclosure, a stereoisomer thereof or a pharmaceutically acceptable salt thereof formulated in a compatible pharmaceutical carrier may also be prepared, placed in an appropriate container, and labeled for treatment of an indicated condition.

In yet another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having an X-ray powder diffraction (XRPD) pattern substantially as shown in FIG. 1.

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity has an X-ray powder diffraction (XRPD) pattern under CuKα radiation substantially as shown in FIG. 1.

In yet another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having a DSC curve substantially as shown in FIG. 2 when subjected to thermal analysis using differential scanning calorimetry (DSC).

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity has a DSC curve substantially as shown in FIG. 2 when subjected to thermal analysis using differential scanning calorimetry (DSC) at a heating rate of 10° C./min.

In another aspect, the present disclosure relates to an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having a TGA curve substantially as shown in FIG. 3 when subjected to thermal analysis using thermogravimetric analysis (TGA).

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity has a TGA curve substantially as shown in FIG. 3 when subjected to thermal analysis using thermogravimetric analysis (TGA) at a heating rate of 10° C./min.

In yet another aspect, the present disclosure relates to an amorphous solid form of compound (S)—N-[5-[1-(3- ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, wherein position and intensity of absorption peak of the amorphous solid form in an infrared (IR) spectroscopy are about as follows:

| Position of Absorption Peak (cm$^{-1}$) | Intensity of Absorption Peak (%) |
|---|---|
| 3404.3 | 72.47 |
| 3287.52 | 71.12 |
| 3084.14 | 77.6 |
| 2979.07 | 71.12 |
| 2930.92 | 69.42 |
| 1757.38 | 47.8 |
| 1701.82 | 23.97 |
| 1589.64 | 41.86 |
| 1557.48 | 49.76 |
| 1517.39 | 45.33 |
| 1443.03 | 66.11 |
| 1394.22 | 57.87 |
| 1372.85 | 58.51 |
| 1331.65 | 44.21 |
| 1298.07 | 31.05 |
| 1261.45 | 41.23 |
| 1240.02 | 40.44 |
| 1137.98 | 40.39 |
| 1090.98 | 51.71 |
| 1027.87 | 62.39 |
| 967.7 | 73.42 |
| 878.04 | 77.11 |
| 810.99 | 79.36 |
| 773.88 | 74.77 |
| 739.68 | 66.93 |
| 641.67 | 76.69 |
| 600.99 | 80.09 |
| 530.58 | 76.64 |
| 499.59 | 75.46 |
| 454.03 | 77.63 |

In some embodiments, an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity has an an infrared (IR) spectroscopy substantially as shown in FIG. 4.

In another aspect, the present disclosure relates to a method for reducing PDE4 activity, comprising administering a therapeutically effective amount of an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide or a therapeutically effective amount of a pharmaceutical composition comprising an amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide to a subject in need thereof, wherein the amorphous solid form has an X-ray powder diffraction (XRPD) pattern substantially as shown in FIG. 1.

The present disclosure will hereinafter be explained in detail in order to better understand the aspects of the present application and its advantages. However, it is to be understood that the following examples are non-limiting and merely illustrative of certain embodiments of the present application.

EXAMPLES

Preparation Examples

Preparation of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide Abbreviations CDI 1,1'-carbonyldiimidazole;
DCM: dichloromethane;
THF: tetrahydrofuran;
TFA: trifluoroacetic acid;
DMAP: 4-(N,N-dimethylamino)pyridine;
TEA: triethylamine;
DMF: N,N-dimethylformamide;
DMSO: dimethylsulfoxide;
HOBt: 1-hydroxybenzotriazole;
DCC: N,N-dicyclohexyl carbondiimide;
TBFA: tetrabutylammonium floride;
EDC.HCl: 1-(3-dimethylaminopropyl)-3-ethyl carbodiimide hydrochloride;
Fmoc: 9-fluorenylmethoxycarbonyl;
MOM: methoxymethyl;
MEM: methoxy ethoxy methyl;
MTM: methylthiomethyl;
SEM: 2-(trimethylsilyl) ethoxy methyl;
TMSE: 2-(trimethylsilyl)ethyl;
DIC: N,N'-diisopropyl carbodiimide;
HOAt: 1-hydroxy-7-azobenzotriazole;
BOP: (benzotriazole-1-yl-oxy-tri-(dimethylamino) phosphonium hexafluoro phosphate);
Cl-HOBt: 6-chloro-1-hydroxy benzotriazole;
DEPBT: 3-(diethoxyphosphoryloxy)-1,2,3-phentriazine-4-one;
HATU: bis(dimethylamino)methylene-triazole[4,5-B]pyridine-3-oxidehexafluorophosphate;
HBTU: benzotriazole-N,N,N',N'-tetramethylurea-hexafluorophosphate;
HCTU: 6-chlorobenzotriazole-1,1,3,3-tetramethylurea-hexafluorophosphate;
HOOBt: 3-hydroxy-1,2,3-phentriazine-4(3H)-one;
PyBOP: hexafluorophosphoric acid benzotriazole-1-yl-oxy tripyrrolidinylphosphine;
TATU: O-(7-azobenzotriazole-1-yl)-N,N,N',N'-tetramethylurea tetrafluoroborate;
TBTU: O-(benzotriazole-1-yl)-N,N,N',N'-tetramethylurea tetrafluoroborate;
OMS: methanesulfonic acid ester;
OTS: p-toluenesulfonic acid ester.

Compound 1

4-methoxy-3-ethoxybenzaldehyde

To a 500 ml three-neck flask equipped with a mechanical stirrer and an inert gas tube were added 30.5 g of isovanillin, 55.2 g of potassium carbonate, 49.9 g of iodoethane and 140 mL of DMF. The mixture was stirred overnight at the room temperature. The mixture was poured into 1400 mL of water, and then the resultant mixture was extracted with ethyl acetate (600 mL×2). The ethyl acetate layers were combined. The organic phase was washed with saturated Na$_2$CO$_3$ (200 mL×3), 200 mL of water and 200 mL saturated NaCl, dried over anhydrous MgSO$_4$, and filtered. The solvent was evaporated to give a straw yellow solid. The solid was recrystallized with a mixed solvent of ethyl acetate and petroleum ether (1:4) to give a white needle crystal (32.9 g). MS (m/z): 181 [M+1]$^+$.

Compound 2

1-(3-ethoxy-4-methoxyphenyl)-2-(methylsulfonyl)-N-(trimethylsilyl)ethylamine

To a 500 mL three-neck flask equipped with a magnetic stirrer and an inert gas tube were added 3.7 g of dimethyl sulfone and 160 mL of THF. The mixture was cooled to −78° C. and 22 mL of n-butyl lithium (2.2 M n-hexane solution) was added dropwise in the mixture. After the addition the mixture was maintained at −78° C. and stirred for 30 min to obtain A. In a 250 mL three-neck flask equipped with a magnetic stirrer and an inert gas tube was added 7.1 g of compound Ta. The flask was cooled in an ice-salt bath. 43 mL of lithium bis-(trimethylsilyl) amide (1.06 M THF solution) was added dropwise in the flask. After the addition the mixture was stirred for 15 min, and then 10 mL solution of boron trifluoride in diethyl ether was added dropwise to the mixture. The resultant mixture was stirred for 5 min to obtain B. B was transferred into A. The mixture was warmed slowly to the room temperature (over about 1.5 hours). The reaction was quenched with 200 mL of 1.6N $K_2CO_3$ solution. The mixture was stirred for 30 min and then separated. The aqueous layer was extracted with ethyl acetate (200 mL×3). All the organic layers were combined. The resultant organic phase was washed with 200 mL saturated NaCl, dried over anhydrous $MgSO_4$ and filtered. The solvent was evaporated to give 10 g of a straw yellow foam solid.

Compound 3

1-(3-ethoxy-4-methoxyphenyl)-2-(methylsulfonyl) ethylamine

To a 500 mL of single-neck flask equipped with a magnetic stirrer were added 10 g of compound 2, 100 mL of diethyl ether and 100 ml of 4N HCl. The mixture was stirred for 30 min at the room temperature and separated. The organic layer was extracted with 4N HCl (100 mL×3). The aqueous layers were combined. The pH of the aqueous phase was adjusted to 12 with 4N sodium hydroxide in an ice bath. The resultant mixture was extracted with ethyl acetate (200 mL×3). The organic layers were combined. The organic phase was washed with 200 mL of saturated NaCl, dried over anhydrous $MgSO_4$ and filtered. The solvent was evaporated. 1.5 g of a white solid was given after purified with column chromatography.

$^1$H NMR (CDCl$_3$): δ 6.93-6.84 (m, 3H), 4.60 (d, 1H, J=8 Hz), 4.12 (q, 2H, J=4 Hz), 3.87 (s, 3H), 3.37-3.21 (m, 2H), 2.92 (s, 3H), 1.86 (s, 2H), 1.48 (t, 3H, J=4 Hz); MS (m/z): 274 [M+1]$^+$; Chiral HPLC (isopropanol/n-hexane/diethylamine=35/65/0.1, Chiralce® OJ-H column, 250×4.6 mm, 1.0 mL/min, @234 nm): 15.2 min (R-isomer, 49.8%), 17.3 min (S-isomer, 50.2%).

Compound 4a (S)-1-(3-ethoxy-4-methoxyphenyl)-2-(methylsulfonyl)ethylamine N-acetyl-L-valine Salt To a 100 mL of single-neck flask equipped with a magnetic stirrer, a reflux-condenser and an inert gas tube were added 6.920 g of compound 3, 2.418 g of N-acetyl L-valine and 50 mL of anhydrous methanol. The mixture was refluxed in an oil-bath for 1 hour, stirred for 3 hours at the room temperature, and filtered in vacuo to give a white solid. The white solid was added in 25 mL of anhydrous methanol. The resultant mixture was refluxed for 1 hour, stirred at the room temperature for 3 hours, and filtered in vacuo to give 6.752 g of a white solid.

Compound 4b (S)-1-(3-ethoxy-4-methoxyphenyl)-2-(methylsulfonyl)-ethylamine

To a 250 mL of single-neck flask equipped with a magnetic stirrer were added 6.752 g of compound 4a, 150 mL of dichloromethane and 150 ml of water. To the mixture was added dropwise 5% sodium hydroxide aqueous solution in an ice bath to adjust pH to 11. The resultant mixture was separated. The aqueous layer was extracted with 150 mL of dichloromethane. The dichloromethane layers were combined. The organic phase was washed with 100 ml of saturated NaCl, dried over anhydrous $MgSO_4$, and filtered. The solvent was evaporated to give 2.855 g of a white solid (99.0% ee). MS (m/z): 274 [M+1]$^+$; Chiral HPLC (isopropanol/n-hexane/diethylamine=35/65/0.1, Chiralcel® OJ-H column, 250×4.6 mm, 1.0 mL/min, @234 nm): 15.2 min (R-isomer, 0.5%), 17.3 min (S-isomer, 99.5%).

Compound 5

3,4-dicyanothiophene

To a 2000 mL of three-neck flask equipped with a magnetic stirrer, a reflux-condenser and an inert gas tube were added 96.8 g of 3,4-dibrominethiophene, 104 g of cuprous cyanide and 100 mL of dried DMF. The mixture was heated at reflux for 4 hours and cooled to the room temperature. To the reaction mixture was added a solution of 400 g of $FeCl_3.6H_2O$ in 700 mL of 1.7N hydrochloric acid. The reaction solution was maintained at 60° C.-70° C. for 30 min. 500 mL of DCM was added to the reaction solution after sufficiently cooled. The resultant mixture was divided into several portions. Each portion is 300 mL and extracted with DCM (300 mL×2). All DCM layers were combined. The extract was divided into several portions. Each portion is 600 mL and washed with 6N of hydrochloric acid (50 mL×2), water, saturated $Na_2CO_3$ aqueous solution and saturated saline solution sequentially, dried over anhydrous $MgSO_4$, and filtered. The solvent was evaporated to give a yellow solid. The yellow solid was washed with a mixed solvent of ethyl acetate and petroleum ether (1:1) and filtered to give 21 g of a white solid. $^1$H NMR (CDCl$_3$): δ 8.07 (s, 2H).

Compound 6 thiophene-3,4-dicarboxylic Acid

To a 500 mL of round-bottom flask equipped with an electromagnetic stirrer and a reflux-condenser were added 15.978 g of compound 5, 43.997 g of potassium hydroxide and 174 mL of ethylene glycol. The mixture was refluxed for 4 hours. After cooling, 350 mL of water was added to the reaction mixture. The resultant mixture was extracted with diethyl ether (100 mL×2). The diethyl ether layers were discarded. An excess amount of concentrated hydrochloric acid was added to the aqueous layer in an ice bath to give a white precipitate. The white precipitate was filtrated and the solid was dissolved in diethyl ether (about 2000 mL). The filtrate was extracted with diethyl ether (300 mL×3). All diethyl ether layers were combined. The organic phase was dried over anhydrous $MgSO_4$ and filtered. The solvent was evaporated to give 15 g of a white solid. The white solid was recrystallized with water. $^1$H NMR (DMSO-$d_6$): δ 10.35 (brs, 2H), 8.17 (s, 2H); MS (m/z): 171 $[M-1]^+$.

Compound 7 thiophene[3,4-c]furan-1,3-diketone

To a 250 mL of round-bottom flask equipped with an electromagnetic stirrer, a reflux-condenser and a drying tube were added 15 g of compound 6 and 120 mL of acetic anhydride. The mixture was refluxed for 3 hours. The solvent was evaporated to give 13 g of a brown solid.

Compound 8

2-nitrothiophene-3,4-dicarboxylic Acid

To a 250 mL of round-bottom flask equipped with an electromagnetic stirrer and a drying tube was added 40 ml of fuming nitric acid (content of 95%). The flask was cooled to 0° C.-5° C. with an ice bath. 10 g of compound 7 was added portionwise (1 g for each portion). After addition the mixture was reacted for 30 min at the current temperature (a yellow solid separated out). The reaction mixture was poured into 80 g of an ice-water mixture. The resultant mixture was extracted with ethyl acetate (100 mL×3). All ethyl acetate layers were combined. The organic phase was washed sequentially with 50 mL×2 of water and saturated saline solution, dried over anhydrous $MgSO_4$ and filtered. The solvent was evaporated to give 10 g of a yellow solid. MS (m/z): 216 $[M-1]^+$.

Compound 9

4-nitrothiophene[3,4-c]furan-1,3-diketone

To a 250 mL of round-bottom flask equipped with an electromagnetic stirrer, a reflux-condenser and a drying tube were added 10 g of compound 8 and 100 ml of acetic anhydride. The mixture was refluxed for 3 hours. The solvent was evaporated to give 9 g of a brown solid.

Compound 10

(S)-1-nitro-5-(1-(3-ethoxy-4-methoxyphenyl)-2-(methylsulfonyl)ethyl)-5H-thiophene[3,4-c]pyrrole-4,6-diketone To a 250 mL of round-bottom flask equipped with an electromagnetic stirrer and a drying tube were added 1.99 g of compound 9, 2.73 g of (S)-1-(3-ethoxy-4-methoxyphenyl)-2-(methylsulfonyl)-ethylamine (compound 4b) and 100 mL of THF. The mixture was stirred overnight at the room temperature. 1.944 g of CDI was added. The resultant mixture was refluxed in an oil-bath for 2 hours. The mixture was cooled to the room temperature in the open air. 200 mL of ethyl acetate and 150 mL of water were added. The mixture was extracted and separated. The organic layer was washed with 100 mL of 0.5N HCl, 100 mL of saturated NaCl, then dried over anhydrous $MgSO_4$ and filtered. The solvent was evaporated. 3.485 g of a light yellow solid was given after purified with column chromatography. MS (m/z): 453 $[M-1]^+$.

Compound 11

(S)-1-amino-5-(1-(3-ethoxy-4-methoxyphenyl)-2-(methylsulfonyl)ethyl)-5H-thiophene[3,4-c]pyrrole-4,6-dione To a 250 mL of round-bottom flask equipped with an electromagnetic stirrer, a reflux-condenser and a drying tube were added 2.27 g of (S)-1-nitro-5-(1-(3-ethoxy-4-methoxyphenyl)-2-(methylsulfonyl)ethyl)-5H-thiophene[3,4-c]pyrrole-4,6-diketone and 100 mL of THF. The mixture was heated at reflux. 1.4 g of reductive powdery iron was added. The resultant mixture was refluxed for 2 hours and filtered in vacuo. The filtrate was evaporated. 200 mL of ethyl acetate and 150 mL of water was added. The mixture was extracted and separated. The organic layer was washed with 100 mL of water, 100 mL of saturated NaCl, then dried over anhydrous $MgSO_4$ and filtered. The solvent was evaporated. 1.53 g of a yellowish-brown solid was given after purified with column chromatography. MS (m/z): 425 $[M+1]^+$.

Compound 12

(S)—N-(5-(1-(3-ethoxy-4-methoxyphenyl)-2-(methylsulfonyl)ethyl)-4,6-dioxo-5,6-dihydro-4H-thiophene [3,4-c]pyrrole-1-yl)acetamide Method I: To a 50 mL of round-bottom flask equipped with an electromagnetic stirrer, a reflux-condenser and a drying tube were added 0.1 g of (S)-1-amino-5-(1-(3-ethoxy-4-methoxyphenyl)-2-(methylsulfonyl)ethyl)-5H-thiophene[3,4-c]pyrrole-4,6-dione, 0.005 g of DMAP and 10 mL of acetic anhydride. The mixture was heated to 60° C. and stirred for 6 hours. The solvent was evaporated. 0.022 g of title compound was given after purified with column chromatography.

Method II: To a 50 mL of round-bottom flask equipped with an electromagnetic stirrer, a reflux-condenser and a drying tube were added 0.1 g of (S)-1-amino-5-(1-(3-ethoxy-4-methoxyphenyl)-2-(methylsulfonyl)ethyl)-5H-thiophene[3,4-c]pyrrole-4,6-dione and 5 mL of pyridine. 0.2 mL of acetylchloride was added dropwise in an ice bath and stirred for 1 hour at the room temperature. The solvent was evaporated. 50 mL of ethyl acetate and 20 mL of water were added. The mixture was extracted and separated. The organic layer was washed with 20 mL of 2N HCl, 20 mL of saturated NaCl, then dried over anhydrous $MgSO_4$ and filtered. The solvent was evaporated. 0.083 g of title compound was given after purified with column chromatography. MS (m/z): 465 $[M-1]^+$. Chiral HPLC (anhydrous alcohol/n-hexane/diethylamine=40/60/0.1, Chiralcel® OJ-H column, 250×4.6 mm, 1.0 mL/min, @230 nm): 9.8 min (R-isomer, 1.2%), 13.8 min (S-isomer, 98.8%). $^1$H NMR (CDCl$_3$): δ 9.27 (s, 1H), 7.30 (s, 1H), 7.07 (s, 1H), 7.05 (s, 1H), 6.81 (d, 1H, J=6 Hz), 5.81 (dd, 1H, J=3 Hz, J=7 Hz), 4.54 (dd, 1H, J=8 Hz, J=11 Hz), 4.08 (q, 2H, J=3 Hz), 3.84 (s, 3H), 3.73 (dd, 1H, J=8 Hz, J=11 Hz), 2.86 (s, 3H), 2.27 (s, 3H), 1.45 (t, 3H, J=5 Hz).

Example 1

Preparation of Amorphous Solid Form 0.266 g of (S)—N-[5-[1-(3-ethoxy-4-methoxyphenyl)-2-(methylsulfonyl)ethyl]-4,6-dioxo-5,6-dihydro-4H-thieno[3, 4-c]pyrrole-1-yl]acetamide was dissolved in 15 mL of ethyl acetate. The mixture was heated to 40° C. and stirred until completed dissolved. After heat filtered, the filtrate was heated to 50° C. and rotary evaporated under vacuum degree of 0.1 MPa. After evaporating to dryness, 0.139 g of white powder solid was given (yield: 52%), i.e., an amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide.

Example 2

X-Ray Powder Diffraction (XRPD)

The experimental parameters of X-ray powder diffraction (XRPD) were as follows: X-ray powder diffraction (XRPD) patterns were obtained by Bruker D8 Advance X-ray powder diffractometer with Cu anode (40 mA, 45 kV). The scanning range was 2θ=2-40°, the step size was 0.02° and the scanning rate was 8°/min.

The X-ray powder diffraction (XRPD) pattern of an amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 was shown in FIG. 1.

As no characteristic peaks were shown in the X-ray powder diffraction (XRPD) pattern, it can be determined that (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 was amorphous.

Example 3

Differential Scanning Calorimetry (DSC) Test

The experimental parameters of differential scanning calorimetry (DSC) were as follows: the heat absorption and release information of the heating of a sample during heating process was obtained by Seiko SII 6220 differential scanning calorimeter (DSC). The heating rate was 10° C./min. Nitrogen was used as protection gas.

The DSC curve of an amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 was shown in FIG. 2.

The baseline of the DSC curve of the amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 2 was not smooth. No obvious heat absorption or release peaks were shown during the heating process.

Example 4

Thermogravimetric Analysis (TGA) Test

The experimental parameters of thermogravimetric analysis method (TGA) were as follows: the weight loss information of a sample during heating process was obtained with Seiko SII 6200 thermogravimetric detector (TG). The heating rate was 10° C./min. Nitrogen was used as protection gas.

The TGA curve of an amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 was shown in FIG. 3.

The weight loss of the amorphous solid formal was 0.5% when the amorphous solid form was heated to decompose.

Example 5

Infrared (IR) Spectroscopy

The experimental parameters of infrared were as follows: PerkinElmer, Spectrum B65.

The infrared (IR) spectroscopy of an amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 was shown in FIG. 4.

The position and intensity of absorption peak of the amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 in an infrared (IR) spectroscopy were about as follows:

| Position of Absorption Peak (cm$^{-1}$) | Intensity of Absorption Peak (%) |
|---|---|
| 3404.3 | 72.47 |
| 3287.52 | 71.12 |
| 3084.14 | 77.6 |
| 2979.07 | 71.12 |
| 2930.92 | 69.42 |
| 1757.38 | 47.8 |
| 1701.82 | 23.97 |
| 1589.64 | 41.86 |
| 1557.48 | 49.76 |
| 1517.39 | 45.33 |
| 1443.03 | 66.11 |
| 1394.22 | 57.87 |
| 1372.85 | 58.51 |
| 1331.65 | 44.21 |
| 1298.07 | 31.05 |
| 1261.45 | 41.23 |
| 1240.02 | 40.44 |
| 1137.98 | 40.39 |
| 1090.98 | 51.71 |
| 1027.87 | 62.39 |
| 967.7 | 73.42 |
| 878.04 | 77.11 |
| 810.99 | 79.36 |
| 773.88 | 74.77 |
| 739.68 | 66.93 |
| 641.67 | 76.69 |
| 600.99 | 80.09 |
| 530.58 | 76.64 |
| 499.59 | 75.46 |
| 454.03 | 77.63 |

Example 8

Dissolution Rate

An amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process in Example 1 was tested.

About 25 mg of the amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide was added to 900 mL of water. The mixture was stirred at a rotating speed of 100/minute at 37° C. for 90 minutes. The supernatant was filtered and diluted. The concentration of the diluted solution (a mg/mL) was determined by ultraviolet spectrophotometer. The dissolution rate was calculated according to the formula 900a/25×100%.

The dissolution rate of the amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide was shown in Table 1.

TABLE 1

Test Results of Dissolution Rate

| Time (min) | Dissolution Rate (%) |
|---|---|
| 0 | 0 |
| 15 | 38.3 |
| 30 | 54.9 |
| 45 | 72.8 |
| 60 | 63.7 |

Example 7

Grinding Stability

An amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process of Example 1 was ground in a glass mortar for 5 minutes. The ground samples were tested with XRPD. The results were shown in Table 4. The results demonstrated that the amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide had good grinding stability.

TABLE 4

Results of Grinding Stability Results

| Original Crystal Form | Grinding Manner | Crystal Form after Grinding |
|---|---|---|
| Amorphous | Grinding in a glass mortar for 5 minutes | Amorphous |

Example 8

Pressure Stability

An amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide was pressed by tablet press machine with single punch. The diameter of the tablet was 6 mm and the hardness was 25-30 N. DSC test was carried out on pressed powder. The DSC curve was substantially identical to the DSC curve as shown in FIG. 2. The result demonstrated that the amorphous solid form has good stability.

Example 9

Hygroscopicity

Hygroscopicity of an amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide was studied. The amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide was placed in a drier containing saturated ammonium chloride solution (RH=80%) until weight was balanced. The crystal form was tested with XRPD.

An amorphous solid form of (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide prepared according to the process of Example 1 was tested. The results demonstrated that the amorphous solid form had good moisture absorption stability.

TABLE 4

Test Results of Hygroscopicity

| Original Crystal Form | Crystal Form after Absorbing Moisture |
|---|---|
| Amorphous | Amorphous |

In the present disclosure, relational terms, such as first and second and the like, are used solely to distinguish one entity or operation from another entity or operation without necessarily requiring or implying any such actual relationship or order between such entities or operations.

From the foregoing it will be appreciated that, although specific embodiments of the present disclosure have been described herein for illustrative purposes, various modifications or improvements may be made by those skilled in the art without departing from the spirit and scope of the present disclosure. Such variations or modifications are intended to fall within the scope of the claims appended hereto.

What is claimed is:

1. An amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide, having an X-ray powder diffraction (XRPD) pattern substantially as shown in FIG. 1.

2. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1, having a DSC curve substantially as shown in FIG. 2 when subjected to thermal analysis using differential scanning calorimetry (DSC).

3. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1, having a TGA curve substantially as shown in FIG. 3 when subjected to thermal analysis using thermogravimetric analysis (TGA).

4. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1, wherein position and intensity of absorption peak of the amorphous solid form in an infrared (IR) spectroscopy are about as follows:

| Position of Absorption Peak ($cm^{-1}$) | Intensity of Absorption Peak (%) |
|---|---|
| 3404.3 | 72.47 |
| 3287.52 | 71.12 |
| 3084.14 | 77.6 |
| 2979.07 | 71.12 |
| 2930.92 | 69.42 |
| 1757.38 | 47.8 |
| 1701.82 | 23.97 |
| 1589.64 | 41.86 |
| 1557.48 | 49.76 |
| 1517.39 | 45.33 |
| 1443.03 | 66.11 |
| 1394.22 | 57.87 |

-continued

| Position of Absorption Peak (cm$^{-1}$) | Intensity of Absorption Peak (%) |
|---|---|
| 1372.85 | 58.51 |
| 1331.65 | 44.21 |
| 1298.07 | 31.05 |
| 1261.45 | 41.23 |
| 1240.02 | 40.44 |
| 1137.98 | 40.39 |
| 1090.98 | 51.71 |
| 1027.87 | 62.39 |
| 967.7 | 73.42 |
| 878.04 | 77.11 |
| 810.99 | 79.36 |
| 773.88 | 74.77 |
| 739.68 | 66.93 |
| 641.67 | 76.69 |
| 600.99 | 80.09 |
| 530.58 | 76.64 |
| 499.59 | 75.46 |
| 454.03 | 77.63 |

5. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1, having an infrared (IR) spectroscopy substantially as shown in FIG. 4.

6. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 that is substantially free of solvent.

7. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 that is substantially free of water.

8. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 that is substantially pure.

9. The amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 that is free of solvent and water.

10. A pharmaceutical composition, comprising the amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 and a pharmaceutically acceptable carrier, diluent or excipient.

11. The pharmaceutical composition of claim 10, formulated as tablet, solution, granule, patch, ointment, gel, capsule, aerosol or suppository administered via parenteral, transdermal, mucosa, nasal, buccal, sublingual or oral route.

12. A process for preparing the amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1, comprising dissolving (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide in ethyl acetate, and rotary evaporating solvent to obtain the amorphous solid form.

13. The process of claim 12, comprising:
dissolving (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide in ethyl acetate until completely dissolved; and
filtering and heating filtrate to 45° C. to 55° C., and rotary evaporated under vacuum degree of 0.1 MPa to obtain the amorphous solid form.

14. A method of treating a disease or condition associated with PDE4 enzyme, preferably meditated by PDE4 enzyme, comprising administering a therapeutically effective amount of the amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 to a subject in need thereof, wherein the disease or condition is selected from the group consisting of an inflammatory disease or condition, an infectious disease or condition, an immune disease or condition, and a cancer disease or condition.

15. The method of claim 14, wherein the subject is a mammal, preferably a human.

16. The method of claim 14, wherein the disease or condition is selected from the group consisting of head carcinoma, thyroid carcinoma, neck cancer, eye cancer, skin cancer, oral cancer, throat cancer, esophagus cancer, breast cancer, bone cancer, leukemia, myeloma, lung cancer, colon cancer, carcinoma of sigmoid, rectal cancer, gastric cancer, prostate cancer, breast cancer, ovarian cancer, kidney cancer, liver cancer, pancreatic cancer, brain cancer, intestinal cancer, heart cancer, adrenal carcinoma, subcutaneous tissue cancer, lymph node cancer, malignant melanoma, malignant glioma, HIV, hepatitis, adult respiratory distress syndrome, bone absorption disease, chronic obstructive pulmonary disease, chronic pneumonia, dermatitis, inflammatory skin disease, atopic dermatitis, cystic fibrosis, septic shock, pyaemia, endotoxin shock, blood dynamic shock, septic disease syndrome, ischemia reperfusion injury, meningitis, psoriasis, fibrosis disease, cachexia, graft rejection of graft versus host disease, autoimmunity disease, rheumatoid spondylitis, arthritis symptom (such as rheumatoid arthritis or osteoarthritis), osteoporosis, Crohn's disease, ulcerative colitis, enteritis, multiple sclerosis, systemic lupus erythematosus, erythema nodosum leprosum of leprosy (ENL), radiation damage, asthma, oxygen enriched lung injury, microorganism infections and microorganism infection syndrome.

17. An amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide with PDE4 inhibitory activity, having an X-ray powder diffraction (XRPD) pattern substantially as shown in FIG. 1.

18. A method for reducing PDE4 activity, comprising administering a therapeutically effective amount of the amorphous solid form of compound (S)—N-[5-[1-(3-ethoxy-4-methoxyphenyl)-2-(methylsulfonyl)ethyl]-4,6-dioxo-5,6-dihydro-4H-thieno[3,4-c]pyrrole-1-yl]acetamide of claim 1 to a subject in need thereof.

19. A method of treating a disease or condition associated with PDE4 enzyme, preferably meditated by PDE4 enzyme, comprising administering a therapeutically effective amount of the pharmaceutical composition of claim 10 to a subject in need thereof, wherein the disease or condition is selected from the group consisting of an inflammatory disease or condition, an infectious disease or condition, an immune disease or condition, and a cancer disease or condition.

20. A method for reducing PDE4 activity, comprising administering a therapeutically effective amount of the pharmaceutical composition of claim 10 to a subject in need thereof.

* * * * *